March 7, 1961 H. C. SWIM ET AL Plant Pat. 2,032
ROSE PLANT
Filed June 16, 1960
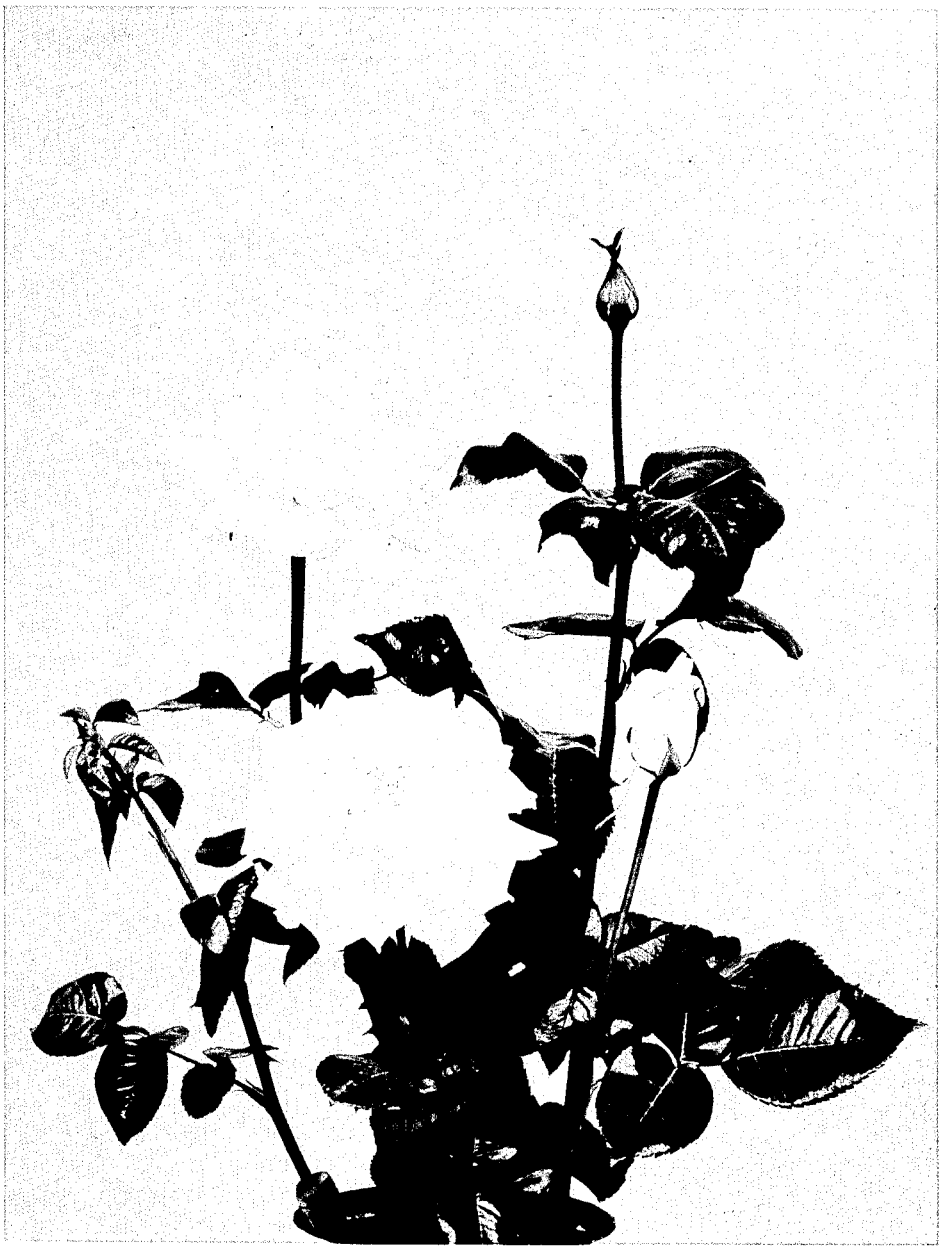
INVENTOR
H. C. Swim and O. L. Weeks
BY Robb & Robb
ATTORNEYS United States Patent Office Plant Pat. 2,032
Patented Mar. 7, 1961

2,032

ROSE PLANT

Herbert C. Swim, Ontario, and O. L. Weeks, Chino, Calif., assignors to The Conard-Pyle Company, West Grove, Pa., a corporation of Pennsylvania Filed June 16, 1960, Ser. No. 36,697

1 Claim. (Cl. 47—61)

The present invention relates to a new and distinct variety of rose plant of the hybrid tea class, which was originated by us by crossing the variety "Virgo" (unpatented) with the variety "Peace" (Plant Patent No. 591).

The primary objective of this breeding was to obtain a new rose variety in which there is combined the best qualities of each of the parent varieties. This objective was fully achieved, along with other desirable improvements, as evidenced by the following unique combination of characteristics which are outstanding in the new variety and which distinguish it from its parents, as well as from all other varieties of which we are aware:

(1) Very large, glossy, leathery, flat foliage of distinctive coloration;

(2) Long, strong and stiff stems which are sufficiently sturdy to always carry the flowers upright;

(3) Attractively formed, long-pointed buds of large size;

(4) Large, double flowers, said flowers having imbricated petals and also having a pronounced tea fragrance; and (5) A distinctive delicate pink general color tonality of the flowers.

In comparison with its seed parent, "Virgo," the large, glossy and leathery foliage of our new variety is clearly differentiated from the non-glossy somewhat thin and small foliage of this parent, while the flower stems of the new variety are stronger and heavier than those of this parent. The flower color of the new variety is also quite different, as well as their large size and double petalage.

As compared with the pollen parent, "Peace," the foliage of our new variety is more flat and the plant has a more upright habit of growth. The flower stems of the new variety are straighter and of substantially greater length, and there is greater imbrication in the petal arrangement and greater doubleness of the flowers of the new variety, as well as a more pronounced fragrange. The flowers of our new variety are a uniform pink color, as distinguished from the dominant yellow edging of the pink color of the parent variety "Peace." The buds of our new variety are also much longer and more pointed than those of this parent.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company Incorporated, of Baltimore, Maryland, except where general color terms of ordinary dictionary significance are obvious:

Type: Hardy; bush; outdoor; seeding; for cut flowers and for garden decoration.

Class: Hybrid tea.

Breeding: Seedling.

*Seed parent.*—"Virgo."

*Pollen parent.*—"Peace."

Propagation: Holds its distinguishing characteristics through succeeding propagations by budding.

*Flower*

Locality where grown and observed: Chino, California.

Flowers borne: Mostly singly to stem; on strong, long stems.

Quantity of bloom: From moderate to free both indoors and in greenhouse.

Continuity: Intermittent.

Fragrance: From moderate to strong. Nature—tea.

Bud:

*Peduncle.*—Long; medium heavy; erect; stiff; entirely smooth. Color—near Moderate Yellow Green, Plate 5GY5/6.

*Before calyx breaks.*—Size—medium. Form—short; pointed; with a conspicuous neck; with foliaceous appendages on the surface of the bud; sometimes with slender foliaceous parts extending beyond the tip of the bud equal to ¼ to ½ of its length. Color—near Moderate Yellow Green, Plate 5GY5/6 (sepals).

*As calyx breaks.*—Color—near Light Yellowish Pink, Plate 2.5YR9/3 (petals).

*As first petal opens.*—Size—large. Form—long; pointed. Color: outside—varying from Pale Purplish Pink, Plate 7.5RP9/2 in center and basal area to Pale Pink, Plate 2.5R9/3 around outer portions; inside—near Brilliant Greenish Yellow, Plate 7.5Y9/8 about point of attachment, this color quickly giving way to Pale Purplish Pink, Plate 7.5RP9/2 in the central portion, and then in turn giving way to Pale Pink, Plate 2.5R9/3 around outer portions of petal. Opening—opens up well; is not retarded or prevented from opening by cold, hot, wet or dry weather.

Bloom:

*Size (when fully open).*—Very large; from 5 to 5½ inches.

*Petalage.*—Very double; usually with no stamens showing; from 40 to 45 petals, plus a few petaloids.

*Form.*—High-centered at first, and remaining more or less high-centered; petals being at first very loosely rolled outward at apical margins but later becoming somewhat more loosely rolled outward at apical margins at maturity.

Petals:

*Texture.*—Thick; soft. Inside—shiny-satiny. Outside—satiny.

*Shape.*—nearly orbicular; entire; somewhat broader than long. Intermediate—obovate-truncate; entire. Inside—obovate; entire; occasionally with one very small notch.

This description of a newly opened flower was made from a rose grown in a greenhouse during March at Chino, California:

*Color.*—Outer petal: outside surface—varying from Pale Purplish Pink, Plate 7.5RP9/2 in center and basal area to Pale Pink, Plate 2.5R9/3 around outer portions; inside surface—near Brilliant Greenish Yellow, Plate 7.5Y9/8 about point of attachment, quickly giving way to Pale Purplish Pink, Plate 7.5RP9/2 in central portion, and in turn giving way to Pale Pink, Plate 2.5R9/3 around outer portion of petal. Intermediate petal: outside surface—varying from Pale Purplish Pink, Plate 7.5RP9/2 in central and basal area to Pale Pink, Plate 2.5R9/3 around outer portions; inside surface—near Brilliant Greenish Yellow, Plate 7.5Y9/8 about point of attachment, fading as it radiates out from the base and giving way to Pale Purplish Pink, Plate 7.5RP9/2 in the central portion, and in turn giving way to Pale Pink, Plate 2.5R9/3 around outer portions. Inner petal: outside surface—near Pale Pink, Plate 2.5R9/3, except very near point of attachment which is near Brilliant Greenish Yellow, Plate 7.5Y9/8, and midrib which is sometimes influenced by a vegetative white streak extending from the base to about midway of the petal length; inside surface—near Brilliant Greenish Yellow, Plate 7.5Y9/8 about point of attachment, fading as it radiates from base and giving way to Pale Purplish Pink, Plate 7.5R9/2 in the central portion, and in turn giving way to Pale Pink, Plate 2.5R9/3 around outer portions.

This description was made from a rose that was open for three (3) days in a greenhouse during March at Chino, California:

*Color.*—Outer petal: outside surface—yellowish white area at base and a more or less obovate pattern, with midrib as central portion, extending about ¾ inch from base, with remainder more or less uniformly Pale Purplish Pink, Plate 7.5RP9/2; inside surface—near Brilliant Greenish Yellow, Plate 7.5Y9/8 about point of attachment, fading to near white and radiating outward from base about ¾ inch, with remainder near Pale Purplish Pink, Plate 7.5RP9/2. Inner petal: outside surface—small yellow to near white area at point of attachment, with remainder between Pale Purplish Pink, Plate 7.5RP9/2 and Light Purplish Pink, Plate 7.5RP8/5; inside surface—near Brilliant Greenish Yellow, Plate 7.5Y9/8 around point of attachment, and slender area of greenish white along midrib to middle of petal, with remainder near Pale Purplish Pink, Plate 7.5RP9/2.

*General color effect.*—Newly opened flower—outer petals Pale Pink, Plate 2.5R9/3, with center portion near Moderate Pink, Plate 2.5R8/5, said central color seeming to be influenced by a glow of yellow which eminates from the base of the petals. 3-days open—outer portion Pale Purplish Pink, Plate 7.5RP9/2, with inner portion near Pale Pink, Plate 2.5R9/3.

*Behavior.*—Drop off cleanly.

*Flower longevity.*—On bush in garden—4 days in October. Cut roses grown in greenhouse and kept at living-room temperatures—4 days in March.

*Reproductive organs*

Stamens: From medium number to many; arranged irregularly about pistils.

Filaments: From medium length to long; most with anthers. Color—reddish.

Anthers: All open at once, more or less. Color—dull yellow.

Pollen: Moderate abundance. Color—yellow.

Pistils: Medium quantity.

Styles: Somewhat uneven; from short to medium length; medium caliper; bunched.

Stigma: Color—whitish yellow.

Ovaries: All enclosed in calyx, generally.

Hips: Globular; smooth.

Sepals: Permanant; moderately short; straight.

Seeds: Medium number; medium size.

*Plant*

Foliage:

*Leaves.*—Compound of 3 to 5 leaflets; normal quantity; very large; heavy; leathery; glossy.

*Leaflets.*—Shape—oval, with apex acute. Base—rounded. Margin—simply serrate.

*Color.*—Mature: upper surface—near Dark Yellowish Green, Plate 2.5G3/3, but with glossy surface; under surface—near a blend of Dark Yellowish Green, Plate 10GY4/5, Moderate Olive Green, Plate 7.5GY4/4 and some lighter shade of greyish yellow green not found in color chart. Young: upper surface—near Moderate Green, Plate 7.5GY5/7, overlaid at midrib and margins especially, and more faintly elsewhere with Dark Purplish Red, Plate 10RP3/10; under surface—all vein netting and midrib are strong Purplish Red, Plate 10RP5/12 which dominates the greyish yellow green so that the latter is unidentifiable.

*Rachis (the supporting stem of the compound leaf).*—Medium caliper. Upper side—grooved; sparsely glandular. Under side—smooth, except for occasional prickle.

*Stipules.*—From moderately short to medium length; moderately narrow; with short points turning out at an angle of 45°.

*Disease resistance.*—More resistant to mildew than most varieties when grown under comparable conditions either outdoors or in greenhouse at Chino, California.

Growth:

*Habit.*—Dwarf; bushy; upright; medium branching.

*Growth.*—Free.

*Canes.*—Moderately heavy.

*Main stems.*—Color—dull grey green. Large prickles—several; long; straight; with short, broad base; color—brown. Small prickles—none. Hairs—none.

*Branches.*—Color—dull grey green. Large prickles—few; long; straight; with long, narrow base; color—dull grey green. Small prickles—none. Hairs—none.

*New shoots.*—Color—center of leaves near Strong Yellow Green, Plate 5GY6/8, with remainder variously overlaid with near Dark Purplish Red, Plate 10RP3/10, giving in combination with the green undertones an almost brownish cast; upper sides of leaf stems strongly marked with Dark Purplish Red, Plate 10RP3/10, giving the new growth in its entirety a bronzy appearance. Large prickles—few; medium length; straight; with long, narrow base; color—light green, with purple tips. Small prickles—none. Hairs—none.

We claim:

A new and distinct variety of rose plant of the hybrid tea class, substantially as herein shown and described, characterized particularly as to novelty by the unique combination of very large, glossy, leathery, flat foliage of distinctive coloration, long, strong and stiff stems of a sturdiness sufficient to always carry the flowers upright, attractively formed, long-pointed buds of large size, large double flowers having imbricated petals and a pronounced tea fragrance, and a distinctive delicate pink general color tonality of the flowers.

No references cited.